United States Patent
Procter et al.

(10) Patent No.: US 11,925,722 B2
(45) Date of Patent: Mar. 12, 2024

(54) COMPOSITION OF A CALCIUM PHOSPHATE AND AN ADDITIVE COMPOUND CONTAINING A PHOSPHATE OR PHOSPHONATE GROUP

(71) Applicant: GPBIO LTD., Limerick (IE)

(72) Inventors: Philip Procter, Divonne les Bains (FR); Michael Pujari-Palmer, Uppsala (SE); Gerard Insley, Limerick (IE); Håkan Engqvist, Uppsala (SE)

(73) Assignee: GPBIO LTD. (IE)

( * ) Notice: Subject to any disclaimer, the term of this patent is extended or adjusted under 35 U.S.C. 154(b) by 607 days.

(21) Appl. No.: 16/767,579

(22) PCT Filed: Nov. 30, 2018

(86) PCT No.: PCT/EP2018/083197
§ 371 (c)(1),
(2) Date: May 27, 2020

(87) PCT Pub. No.: WO2019/106173
PCT Pub. Date: Jun. 6, 2019

(65) Prior Publication Data
US 2020/0384147 A1    Dec. 10, 2020

(30) Foreign Application Priority Data

Dec. 1, 2017 (SE) .................................... 1751483-7

(51) Int. Cl.
| | |
|---|---|
| *A61K 6/838* | (2020.01) |
| *A61K 6/58* | (2020.01) |
| *A61L 24/02* | (2006.01) |
| *A61L 27/12* | (2006.01) |
| *A61L 27/36* | (2006.01) |
| *A61M 5/19* | (2006.01) |

(52) U.S. Cl.
CPC ............... *A61L 24/02* (2013.01); *A61K 6/58* (2020.01); *A61K 6/838* (2020.01); *A61L 27/12* (2013.01); *A61L 27/365* (2013.01); *A61M 5/19* (2013.01); *A61L 2400/06* (2013.01); *A61L 2430/12* (2013.01); *A61L 2430/34* (2013.01)

(58) Field of Classification Search
None
See application file for complete search history.

(56) References Cited

U.S. PATENT DOCUMENTS

| | | |
|---|---|---|
| 4,612,053 A | 9/1986 | Brown et al. |
| 2010/0121459 A1 | 5/2010 | Garigapati et al. |
| 2011/0318835 A1 | 12/2011 | Chen et al. |
| 2012/0010599 A1 | 1/2012 | Jin et al. |
| 2013/0309214 A1* | 11/2013 | Fazan ..................... A61L 24/02 |
| | | 514/16.7 |
| 2016/0158416 A1 | 6/2016 | Yun |

FOREIGN PATENT DOCUMENTS

| | | |
|---|---|---|
| CN | 105133022 | 12/2015 |
| EP | 2866856 A1 | 5/2015 |
| JP | 2010 075247 | 4/2010 |
| WO | WO 2014/004211 | 1/2014 |

OTHER PUBLICATIONS

Ennor, A. and L. Stocken, Biochemical Journal 43: 190-191 (1948). (Year: 1948).*
Kvam, B., et al., Magnetic Resonance in Medicine 25: 355-361 (1992). (Year: 1992).*
Yang, L., et al., PNAS 111: 12097-12102 (2014). (Year: 2014).*
International Search Report for PCT/EP2018/083197, dated Feb. 15, 2019, 2 pages.
Kaneno et al., "Synthesis and Characterization of Calcium Phosphate-AMP Layered Materials", Key Engineering Materials vols. 317-318 (Aug. 2006) pp. 769-772.

* cited by examiner

*Primary Examiner* — David J Blanchard
*Assistant Examiner* — Daniel F Coughlin
(74) *Attorney, Agent, or Firm* — Quarles & Brady LLP

(57) ABSTRACT

The present invention relates to a composition of a calcium phosphate such as tetracalcium phosphate or α-TCP and an additive compound selected from nucleic acid or nucleotides, phospho(enol)pyruvic acid and phosphocreatine. The composition may be used as a tissue adhesive.

11 Claims, 5 Drawing Sheets

Cure time before exposure to liquid

| Cure time | Shear strength (N/cm2) |
|---|---|
| 6 | 124.2257644 |
| 12 | 236.3674951 |
| >1000 | 167.2073276 |

Figure 6.

CaP type

| CaP Type | Shear strength (N/cm2) |
|---|---|
| TCP | 236.37 |
| TTCP | 31.85 |
| CaSi | 14.92 |

Figure 7.

COMPOSITION OF A CALCIUM PHOSPHATE AND AN ADDITIVE COMPOUND CONTAINING A PHOSPHATE OR PHOSPHONATE GROUP

CROSS-REFERENCE TO RELATED APPLICATION

This application claims priority to and is a 35 U.S.C. § 371 national phase application of PCT/EP2018/083197, filed on Nov. 30, 2018, entitled "COMPOSITION OF A CALCIUM PHOSPHATE AND AN ADDITIVE COMPOUND CONTAINING A PHOSPHATE OR PHOSPHONATE GROUP", which application claims priority to and the benefit of Sweden Patent Application No. 1751483-7, filed Dec. 1, 2017, the disclosures of which are incorporated herein by reference in their entirety.

FIELD OF THE INVENTION

The present invention relates to a composition of calcium phosphate and an additive compound containing a phosphate or phosphonate group. The additive compound is selected from a nucleic acid or nucleotides, phospho(enol)pyruvic acid and phosphocreatine. Since the composition exhibits unexpected adhesive properties it may be used as an adhesive. The invention further relates to a method of treating tissue, and to a kit.

BACKGROUND

Calcium phosphates (CaP) and in particular hydroxyapatite ($Ca_{10}(PO_4)_6(OH)_2$, HA), is a mineral that is widely used in medical applications due to its similarity to the mineral components of bone and teeth and its biocompatibility. Furthermore hydroxyapatite is non-toxic, biocompatible and bioactive. This means that hydroxyapatite is not harmful and not recognized as a foreign body and on the other hand that it may have positive effects on remodelling of bone. Hence hydroxyapatite has been widely used in bone repair and as drug/gene delivery vehicle, catalyst, ion adsorption/exchange agent, photoelectric reagent and so on.

The field of biomaterials includes fixation of implants to tissues as well as tissue repair. The limited mechanical strength of implants in combination adhesives has remained an issue within the field of implants and biomaterials. The repair of soft tissues or internal organs with adhesives has also been broadly unsuccessful.

US2012288446 (US'446) discloses an adhesive comprising a multivalent metal compound, a compound comprising a phosphoserine oligomer or a phosphoserine capped polymer wherein the latter compound is present at 10-90 wt. %. US'446 discloses experimental data using tetra calcium phosphate (TTCP) as the multivalent metal compound and phosphoserine-ethyleneglycol-diglycidyl-phosphoserine for example and obtains adhesive strength of up to 3.76 MPa when adhered to bone.

US20130122057 (US'057) discloses a bone restorative composition comprising amino acid phosphate species, a multivalent metal compound and a bioactive glass material containing ionic functional groups. US'057 disclose examples using a composing comprising TTCP as the multivalent metal compound and phosphoserine together with various amounts of Combeite Bioactive glass and water and adhere it to bone. The shear strengths obtained varied between 0.75-2.13 MPa.

U.S. Pat. No. 8,765,189 (US'189) teaches an adhesive composition comprising a multivalent metal compound and a phosphoserine like compound in an amount of 10-90 wt %. US'189 disclose an adhesion shear strength to cortical bone after 5 minutes of 130-890 kPa when using TTCP as the multivalent metal compound and various phosphorylated compounds and 650 kPa when using α-TCP and phosphoserine.

Even though there are several tissue adhesives available today on the market none of them are ideal sealants or even adhesives. Cyanoacrylates have shown good adhesion but have shown inflammatory response during degradation. Fibrin glues have low adhesive strength but are more biocompatible. Other adhesives struggle with high costs and long curing times or the lack of tailoring the curing time dependent on the tissue and the situation. Soft tissue adhesive usually contain fibrin or gelatin other various polysaccharides.

Still there is a need for new and improved adhesive compositions.

SUMMARY OF THE INVENTION

The aim of the present invention is to overcome the drawbacks of the prior art. Therefore in a first aspect the present invention relates to an aqueous composition comprising:
a. an aqueous solution,
b. a calcium phosphate compound
c. an additive compound selected from a phosphonated nucleic acid or phosphonated nucleotides, phospho(enol)pyruvic acid and phosphocreatine, wherein the carboxylic acid of the phospho(enol)pyruvic acid and phosphocreatine may be in acid form or the corresponding salt;
wherein the calcium phosphate compound represents 10-90 wt % and the additive compound represents 10-90 wt % of the solid content in the composition,
wherein the composition comprises an acid, said acid optionally being the carboxylic acid of the additive compound, and has an acid concentration of 1.0-4.0M, and
wherein the L/P ratio is 0.16-0.45.

In a second aspect the present invention relates to a biological tissue adhesive.

In a third aspect the present invention relates to a bone filler.

In a fourth aspect the present invention relates to a dental implant.

In a fifth aspect the present invention relates to the use of the aqueous composition adhering soft tissue to hard or soft tissue.

In a sixth aspect the present invention relates to the use of the aqueous composition for adhering an implant or a scaffold to a tissue wherein the implant or scaffold is made of metal, polymeric material, ceramic or tissue-derived products such as collagen, matrigel, autologous blood, platelet rich plasma or demineralized bone.

In an seventh aspect the present invention relates to the use of the aqueous composition for strengthening sealed or repaired tissue.

In an eight aspect the present invention relates to a method of adhering a first tissue to a second surface using the tissue adhesive according to the present invention comprising:
a. applying the tissue adhesive according to the present invention to the first tissue or to the second surface and optionally leave it for a suitable period of time;

b. bringing the first tissue and the second surface into contact with each other;

c. optionally applying a pressure on the first and second tissue for a suitable period of time; and d. letting the tissue adhesive cure.

In a ninth aspect the present invention relates to a kit for preparing the composition according to the present invention comprising at least two containers wherein any one container in the kit can contain any of the aqueous solution, the additive compound, the calcium phosphate compound or a combination thereof, with the proviso that both the additive compound and the calcium phosphate compound cannot be present in the same container as the aqueous solution; and wherein the amount of aqueous solution, additive compound, calcium phosphate compound in the containers is such that when mixed the composition according to the present invention is obtained.

In a tenth aspect the present invention relates to a syringe comprising at least two compartments wherein any one compartment in the kit can contain any of the aqueous solution, the additive compound, the calcium phosphate compound or a combination thereof, with the proviso that both the additive compound and the calcium phosphate compound cannot be present in the same container as the aqueous solution; and wherein the amount of aqueous solution, additive compound, calcium phosphate compound in the containers is such that when mixed the composition according to the present invention is obtained; and wherein the syringe further comprises a mixing device configured to mix the components of the at least two compartments.

In an eleventh aspect the present invention relates to a composition according to the present invention for use in the treatment of scar tissue or in the treatment of damaged soft tissue or in the treatment if damaged hard tissue.

In a twelfth aspect the present invention relates to a composition for use in the creation of medical and industrial cements and ceramics. The ultimate form of the present invention is as a hard composite material that is a majority (by weight) ceramic.

In a thirteenth aspect the present invention relates to a composition for use in the hard tissue engineering. This could be for growing bone tissue outside the body, as a scaffold. In the field of tissue engineering cells can be grown into tissue-like constructs using scaffolds. The present invention displays multiple properties that are advantageous as a scaffold material (i.e. stiffness similar to calcified issues, similar chemistry and surface properties, similar cell interactions, etc.).

In a fourteenth aspect the present invention relates to a composition according to the present invention or use of a composition according to the present invention in the adhesion of tissue engineered scaffolds. The adhesion is a hybrid material, rather than solely a biomaterial or tissue. The present invention would allow smaller tissue engineered constructs to be glued, and assembled into successively large constructs. This addresses an unsolved problem in the field because large tissue constructs cannot be grown using currently available methods because the diffusion of nutrients into growing tissues/tissue constructs is limited to <1 mm. The present invention would allow small tissue constructs to be assembled prior to implantation, or in ways that overcome the diffusion limit (i.e. by assembling and gluing together tissue construct pieces to include vascularity (blood vessels) or instruments that will transport and distribute nutrients to the internal surfaces of the aggregated tissue constructs.

All the embodiments presented herein relates to all the aspects of the present invention.

BRIEF DESCRIPTION OF THE FIGURES

FIG. 6. Adhesive strength by cure time prior to submersion in liquid. Samples were allowed to cure for 6, 12, or >1000 minutes prior to submerging into liquid (water), 37° C. Cortical shear (for bone-to-bone adhesion) after 16-24 hours of cure time.

FIG. 7. Adhesive strength by type of calcium salt. Cortical shear adhesive strength (for bone-to-bone adhesion) by calcium salt type (Calcium silicate (Portland cement, CaSi), tricalcium phosphate (TCP), or tetracalcium phosphate (TTCP)), with 25% phosphocreatine (wt %) and 75% calcium salt (wt %), and liquid to powder ratio of 0.25 for TTCP and CaSi and 0.20 for α-TCP, after curing 16-24 hours in 100% humidity, 37° C.

DETAILED DESCRIPTION OF THE INVENTION

Figure 1:
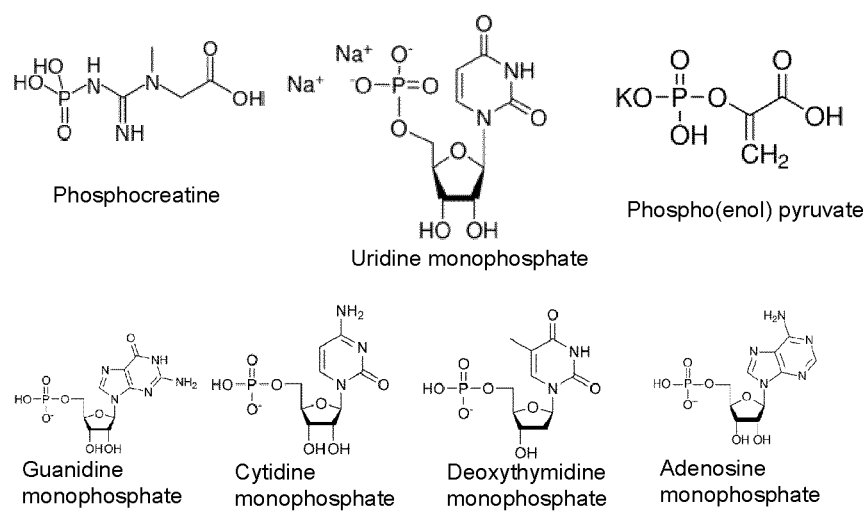
FIG. 1. Schematic view of the chemical structure of phosphocreatine, uridine monophosphate and phospho(enol)pyruvate.

In the present application the word "aqueous solution" also encompasses water and water of any purity. The water may be but is not limited to tap water, distilled water or deionized water or ionized water. The aqueous solution may also be a buffer such as PBS or any suitable saline buffer. The aqueous solution may also contain acidifying or alkaline agents, such as citric acid and hydrochloric acid.

The Composition

The composition according to the present invention is an aqueous composition comprising an aqueous solution, a calcium phosphate and an additive compound selected from nucleic acid or nucleotides, phospho(enol)pyruvic acid (an alpha keto acid) and phosphocreatine. The additive compound comprises a phosphate group or a phosphonate group. The carboxylic acid of the phospho(enol)pyruvic acid and phosphocreatine may be in the acid form or as the corresponding salt. For example the salt may be the sodium or potassium salt of the corresponding acid. The phosphate or phosphonate groups may be in protonated (acid) form or as a salt. For example the salt may be the sodium or potassium salt of the corresponding acid. In one embodiment the additive compound is selected from the group consisting of uridine monophosphate, inosine-5-monophosphate, uridine- 5-monophosphate, phospho(enol)pyruvic acid or phosphocreatine, preferably phosphocreatine.

The present inventors have found that this composition provides good mechanical strength and easy handling which makes the composition suitable as a tissue adhesive.

The calcium phosphate compound may be any suitable compound and may be selected from mono-, di-, tri-, tetra- or octacalcium phosphate, amorphous calcium phosphate and hydroxyapatite. In one embodiment the calcium phosphate is tricalcium phosphate such as α-TCP. The calcium phosphate compound may be used in any form or shape but is preferably in form of a powder having a mean particle size of 5-5000 nm. The particles may be spherical, in the shape of flakes, or granular.

Without being bound by theory it is believed that the additive compound acts as a curing agent providing improved mechanical strength to the composition. The amount of additive compound should be 10-90 wt % of the solid content. In one embodiment a preferred amount of the additive compound is 25-75 wt % preferably 25-50 wt % such as 25 wt %, 50 wt % or 75 wt %. In order to balance the different properties of the inherent components of the composition the amount of additive compound may depend on amount of calcium phosphate and possible accelerators or retardants such as sodium citrate. The amount of additive may differ depending on the type of additive.

The composition comprises an aqueous solution in such an amount that the liquid to powder ratio (L/P) is 0.16-0.45 preferably 0.20-0.42 or 0.23-0.42. Powder means the calcium phosphate plus the additive compound and the ratio is a volume (mL) to weight (g) ratio. The water may be distilled or deionized water or ionized water or any water of high purity but tap water may also be used. The aqueous solution may also be in the form of a hydrogel such as hyaluronic acid, polyvinyl alcohol, chitosan, collagen or a combination thereof. By using a hydrogel as the aqueous solution the composition may more easily remain at the wanted location during curing.

When the additive compound is nucleic acid or nucleotides the L/P ratio may be 0.25-0.42 preferably 0.33-0.42 more preferably around 0.35. When the additive compound is phospho(enol) pyruvic acid the L/P ratio may be 0.30-0.40 preferably 0.33 to 0.35 more preferably around 0.35 and when the additive compound is phosphocreatine the L/P ratio may be 0.15-0.40 preferably 0.20-0.35 more preferably 0.20-0.30 and even more preferably 0.25-0.30.

The additive compound may be in acid form or in salt form such as sodium or potassium salt. When the additive compound is in salt form the composition comprises an added acid such as hydrochloric acid or acetic acid. The acid concentration of the acid may be 1-4M such as 1.5 to 4M. The function of the acid is to create an acid/base reaction, and to assist with dissolution since the adhesive needs an acid and a base to react. The concentration of the acid is preferably high, since the amount of liquid is very small, and the needed acidity must be low (pH wise).

An advantage of the present invention is that the curing time may be tailored so that it cures at the right moment. This is dependent on the application. Sometimes the composition should cure very rapidly and sometimes the composition should be mixed or shaped for a while and when applied it might need some adjustment and therefore the curing should be postponed.

A retardant such as sodium citrate may be added to the reaction mixture and the amount may be 5-66% (weight/volume). In one embodiment the amount is 16-33% (weight/volume) such as 22%. The retardant may be but is not limited to sodium citrate (monosodium, di-sodium or tri-sodium citrate) or citric acid. Additional retardants include sodium malonate, sodium succinate, sodium tartarate, and sodium pyrophosphate. The composition may further comprise additives such as growth factors, nutrients, anti-oxidants and so on. But the composition works without retardants and in one embodiment at least 95 wt %, such as at least 98 wt %, or at least 99 wt %, of the solid content of the composition comprises a calcium phosphate and additive compound and optionally an acid.

Preparing and Curing of the Composition

The composition is formed by mixing the solid components calcium phosphate and the additive compound and an optional accelerator or retardant with the aqueous solution.

Preparing the composition may be done by premixing calcium phosphate and the additive. The mixing may be done by stirring, kneading or shaking using any suitable means. The aqueous solution is then added and the obtained mixture is mixed.

The curing may be done at any suitable temperature. In one embodiment the mixing is done at room temperature or below, 10-25° C., and kept at 25° C. or lower, such as 10-20° C. After applying the composition the curing temperature is preferably increased to 37° C. or higher.

Curing of the composition will occur when mixing the solid components calcium phosphate and the additive compound with the aqueous solution. The curing reaction will lead to the formation of a thick paste and ultimately a solid cement. The formed cement may even be transparent.

The composition according to the present invention may have a shear strength to bone of at least 0.4 MPa, or at least 0.6 MPa, or at least 0.8 MPa, or at least 1 MPa, or at least 1.4 MPa when measured after 16-24 h of curing at 100% humidity and 37° C.

Applications

The composition according to the present invention may be used for a variety of applications such as the treatment of damaged or scar tissue. Due to the ease of applying the composition and the mechanical strength of the cured composition the composition may be used as an adhesive for biological tissue. By applying the composition to soft tissue another soft tissue or the same soft tissue may be adhered and a sufficient mechanical strength is formed between the two soft tissues. The soft tissue may be selected from but is not limited to tendon, ligament, cartilage, fascia, skin, fibrous tissue, muscle, fat, nerve, blood vessel, liver, stomach, intestines, bladder, brain, eyes, uterus, lungs, esophagus, heart, lung, kidney, spleen and glands. In one embodiment the soft tissue is selected from fascia, skin, fibrous tissue, muscle, fat, nerve, blood vessel, liver, stomach, intestines, bladder, brain, eyes, uterus, lungs, esophagus, heart, lung, kidney, spleen and glands. In one embodiment the soft tissue is cartilage or tendon. In one embodiment the soft tissue is a tissue having an extra cellular matrix, collagen and elastin. In another embodiment the soft tissue is a tissue having an epithelium. The tissue may also be a hard tissue such as bone or tooth.

Various implants and fillers may comprise the composition according to the present invention. For example a bone filler may comprise the composition and optionally also other biologically active materials such as growth factors. The composition may be applied to any bone void in order to fill the void, secure or anchor an implant or to stabilize a fracture. Dental implants such as a crown, bridge, denture, screw, root filler or anchoring material may also comprise the composition according to the present invention.

An implant or a scaffold may also be adhered to a tissue by using the composition according to the present invention. The implant or scaffold may be made of synthetic or biological material or a combination thereof. Synthetic materials may be metal, polymers or ceramics where the metals may be titanium, niobium or alloys of the same or aluminum oxide, stainless steel, where the polymers may be polyurethane, polyesters (e.g. polylactic acid, polyglycolic acid, polycaprolactone), polyacrylates (e.g. polymethyl methacrylate, poly(2-hydroxyethyl methacrylate)), polyethers (e.g. polyethylene glycol), polysiloxanes, hydrogels (e.g. polyvinyl alcohol) and polyvinyls (e.g. polyethylene, polypropylene, polyisbutylene, polystyrene) and where the ceramics may be calcium phosphates (e.g. hydroxyapatite, monetit, tetra calcium phosphate), metal oxides (e.g. aluminum oxides, zirconium oxides, titanium oxides) or bioglass. Biological materials may be but is not limited to collagen, hyaluronic acid, chitosan, cells, tissue, decellularized tissue, platelet rich plasma, Matrigel®, demineralized bone, fibrin, cellulose, synthetic or natural silk etc. The material may be in the shape of particles, fibres or a solid surface.

During the healing process after treating damaged tissue the tissue or the scar lacks the sufficient mechanical strength and the repaired tissue may leak body fluids. The present invention may be used to further strengthen the tissue during healing or scar formation and may even be used to seal the tissue in order to minimize leakage of body fluids. For example in combination with sutures the present composition may be added to the tissue section to be sutured together in order to provide further strength and sealing.

Adhering of a first tissue to a second surface may be done by applying the tissue adhesive or the composition according to the present invention to the first tissue. This may for example be two or more tissues or a tissue to a surface such as an implant or scaffold. The composition may also be applied to the second surface as well. The adhesive may be left for a suitable period of time before bringing the two or more tissues or surfaces into contact with each other. The time is dependent on content of the adhesive and the curing time and also on the tissues or materials but non-limiting examples are 10 seconds or longer, or 30 seconds or longer, or 1 minute or longer, or 5 minutes or longer. In one embodiment the composition is left for 20 seconds to 60 seconds before bring the two or more tissues or surface into contact with each other. The surfaces are then brought into contact with each other and if necessary pressure may be applied. The pressure is applied depending on the tissue/material and the cure time of the composition but non-limiting examples are 10 seconds or longer, or 30 seconds or longer, or 1 minute or longer, or 5 minutes or longer. In one embodiment a pressure is applied for 1-3 minutes. In order to cure the composition faster energy may be applied to the composition or to the part of the tissue to which the composition have been applied. This may be done by applying UV, heat or radiation of any suitable type for a couple of seconds up to minutes. The adhesive or the composition is then left to cure to the final cured composition. The adhesive may be fully cured after 5 minutes up to 48 hours depending on the composition and the tissue or surface.

The curing time is dependent on the ratios of the inherent components however due to that the composition starts to cure when mixed the composition is mixed together at a suitable time prior to use or application. In certain applications the composition should cure rapidly after application of the composition and in other applications a slower curing is wanted. The present invention facilitates tailoring of the curing time so that the user may prepare the composition on beforehand without having a fully cured composition when it is time to apply it or prepare it to obtain a composition that is still shapeable or to prepare a composition that cures almost instantly.

The method may be performed in vivo or in vitro but some of the steps may be done in vitro followed by steps done in vivo. For example pieces of bone may be adhered to each other using the composition or adhesive according to the present invention and cured in vitro before put in place in vivo. Injuries that require replacement of large pieces of bone (>2-20 mm) are unable to heal without intervention. Such large pieces of bone cannot currently be grown for implantation because oxygen and nutrients cannot penetrate deeper than 500 um-2 mm. One example of a solution to this problem is to grow multiple smaller pieces of bone and to adhere them together (in vitro or ex vivo), immediately prior to implantation in vivo by using the composition according to the present invention. Tissue engineered constructs, such as bone scaffolds, are often limited by size because vascular channels that allow oxygen and nutrients to properly penetrate large constructs cannot be printed, carved or created easily. One example of a solution is to print smaller modules or pieces of a large construct and to grow them individually before assembling into increasingly larger constructs, in vitro, via an adhesive according to the present invention. The final construct can then be implanted, in vivo, following a suitable acclimation and growth period in vitro.

Screw augmentation is employed when weakened or injured bone requires reinforcement, often with metal plates, wires, or other orthopaedic fixation devices. A significant unresolved challenge in the field is fixation of poor quality bone. A bone adhesive could increase the screw-bone bond strength, especially in weak bone, over currently available augmentation agents (poly-methyl-methacrylate (PMMA) derivatives and calcium phosphates) because neither are successful at forming strong bonds with bone.

The working time can be broken into three phases: The mixing and tacky phase, the dough phase and the final cured phase. During the mixing and tacky phase the mixture is easily mixed and flows with minor resistance. The preferred application period is near the end of the tacky phase and beginning of the dough phase. The dough phase is characterized by an increase in cohesion and decrease in adhesion. During the dough phase adhered tissue can be easily rearranged, aligned or even separated and reattached with minor effect on the final bond strength. However, during the dough phase application of the thickened and more cohesive mixture can be more difficult, thus the tacky phase is the preferred application period, while the dough phase is the preferred time for rearrangement. Finally, during the final cure phase the adhesive no longer moves easily, if at all, and revisions may significantly affect final bond strength.

Kit for Preparing the Composition

A kit comprising the different components of the composition may be used to prepare the present composition. The kit may comprise at least two containers where the containers may be any suitable type of container such as a bowl, bag, dish, plate, beaker, flask, tin, cup or bottle and may be of any size and shape. Any one container in the kit can contain any of an aqueous solution, calcium phosphate and the additive compound and the optional compounds such as accelerators or retardants, with the proviso that both the additive compound and calcium phosphate cannot be present in the same container as the aqueous solution. In other words one container may comprise the aqueous solution while a second or additional container may comprise the solid components (the additive compound and calcium phosphate), or one container may comprise the aqueous solution and one of the solid components and the second container comprises the other two solid components, or one container comprises the aqueous solution and one of the solid components and the second container comprises the aqueous solution and the other two components (with the proviso that the other two components are not calcium phosphate and the additive). In one embodiment the kit comprises three or more containers. The amount of aqueous solution, additive compound and calcium phosphate in the containers is such that when mixed the composition according to the present invention.

The kit may also be in form of a syringe having at least two compartments. The compartments in the syringe can contain any of an aqueous solution, the additive compound and calcium phosphate and the optional compounds such as accelerators or retardants. However both the additive compound and the calcium phosphate cannot be present in the same compartment as the aqueous solution. In other words one compartment may comprise the aqueous solution while a second or additional compartment may comprise the solid components (the additive compound and the calcium phosphate), or one compartment may comprise the aqueous solution and one of the solid components and the second compartment comprises the other two solid components, or one compartment comprises the aqueous solution and one of the solid components and the second compartment comprises the aqueous solution and the other two components (with the proviso that the other two components are not the calcium phosphate and the additive). In one embodiment the kit comprises three or more compartments. The amount of aqueous solution, additive compound and calcium phosphate in the compartments is such that when mixed the composition according to the present invention.

The syringe further comprises a mixing device that is configured to mix the components of the compartments during application of the components. The mixing device may be arranged at the tip of the syringe or within the compartments.

EXAMPLES

Here below are examples of the preparation and testing of composition according to the present invention. Compositions having various L/P ratios as well as different contents of additive compound and calcium phosphate have been tested and have been prepared according to the same procedure as described below. The results are seen in the accompanying figures.

Compositions were prepared by premixing the calcium salt α-TCP powders (0.06 g, with 90% of particle size distribution below 75 μm) and phosphocreatine (0.02 g) and by stirring with a spatula. Distilled water (0.016 ml, 16.66 wt % of the total weight) containing 22% (w/v) retardant sodium citrate was then added to the premixture and mixed by stirring for 10-20 seconds. L/P 0.20.

The composition was spread onto a cortical cube surface (1 cm×1 cm), to approximately 0.1-1 mm thickness with a spatula, sealed with manual clips, and stored in a humid sealed container kept at 37° C., within 60 seconds of adding the liquid. The mechanical testing was done using a Shimadzu AGS-X machine, with trapezium liteX software, at a crosshead speed of 1 mm/minute. After testing the surface area of each cube that was covered with adhesive was measured with calipers and the recorded peak force was divided by the surface area to produce force per surface area (N/cm2).

Figure 2:
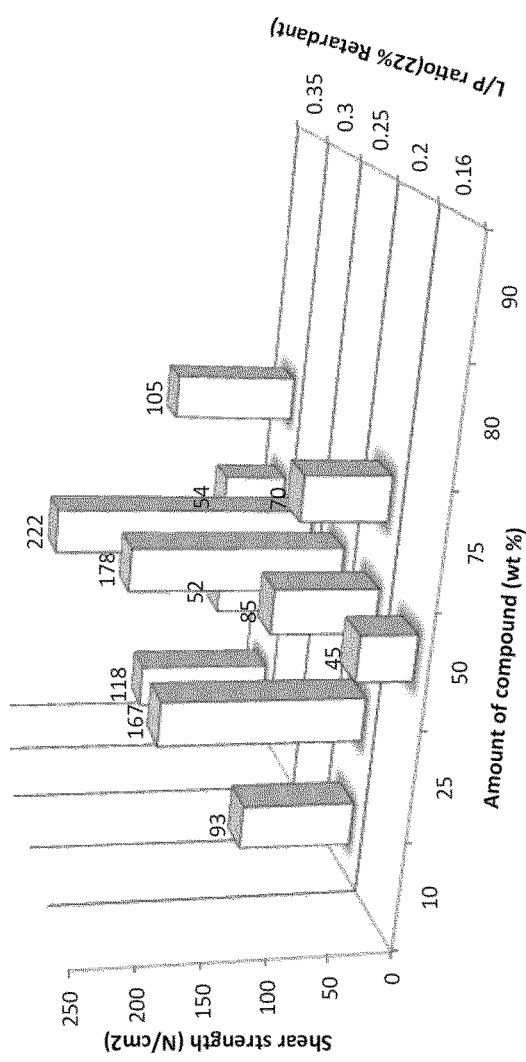
FIG. 2. Chemical composition chart (hard tissue). Cortical shear adhesive strength (for bone-to-bone adhesion) by phosphocreatine content (wt %) and water content (L/P ratio), after 16-24 hours in 100% humidity, 37° C.

The results are disclosed in FIG. 2.

Compositions were prepared by premixing the calcium salt α-TCP powders (0.06 g, with 90% of particle size distribution below 75 μm) and Uridine monophosphate nucleotide (0.020 g) and by stirring with a spatula. Distilled water (0.016 ml, 20.00 wt % of the total weight) containing hydrochloric acid (4 molar) was then added to the premixture and mixed by stirring for 10-20 seconds. L/P of 0.2.

The composition was spread onto a cortical cube surface (1 cm×1 cm), to approximately 0.1-1 mm thickness with a spatula, sealed with manual clips, and stored in a humid sealed container kept at 37C, within 60 seconds of adding the liquid. The mechanical testing was done using a Shimadzu AGS-X machine, with trapezium liteX software, at a crosshead speed of 1 mm/minute. After testing the surface area of each cube that was covered with adhesive was measured with calipers and the recorded peak force was divided by the surface area to produce force per surface area (N/cm2).

Figure 3:
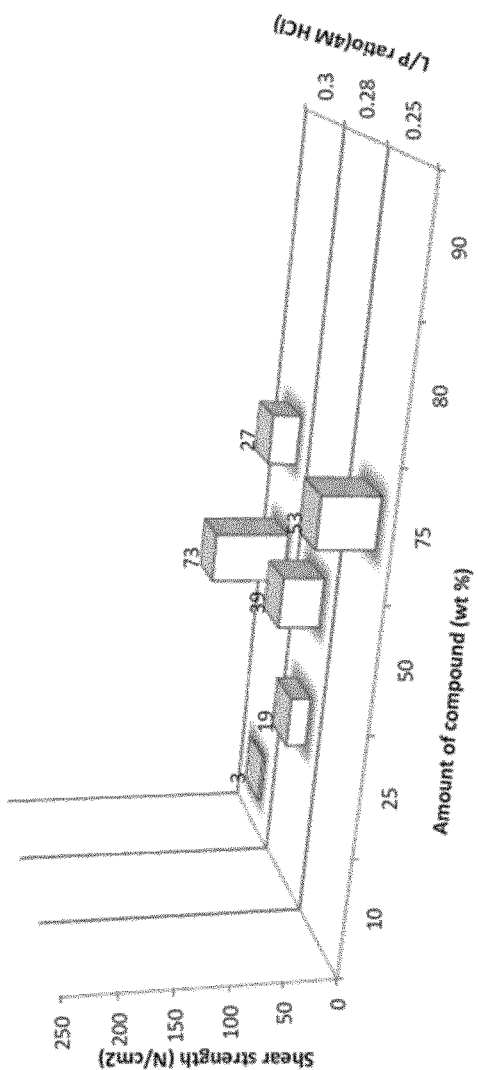
FIG. 3. Chemical composition chart (hard tissue). Cortical shear adhesive strength (for bone-to-bone adhesion) by nucleotide content (Uridine monophosphate) (wt %) and water content (L/P ratio), after 16-24 hours in 100% humidity, 37° C.

The results are disclosed in FIG. 3.

Compositions were prepared by premixing the calcium salt α-TCP powders (0.06 g, with 90% of particle size distribution below 75 μm) and a mixture of small chain length and individual nucleotides (0.02 g) and by stirring with a spatula. Distilled water (0.028 ml, 25.9 wt % of the total weight) was then added to the premixture and mixed by stirring for 10-20 seconds. L/P ratio of 0.35.

The composition was spread onto a cortical cube surface (1 cm×1 cm), to approximately 0.1-1 mm thickness with a spatula, sealed with manual clips, and stored in a humid sealed container kept at 37C, within 60 seconds of adding the liquid. The mechanical testing was done using a Shimadzu AGS-X machine, with trapezium liteX software, at a crosshead speed of 1 mm/minute. After testing the surface area of each cube that was covered with adhesive was measured with calipers and the recorded peak force was divided by the surface area to produce force per surface area (N/cm2).

Figure 4:
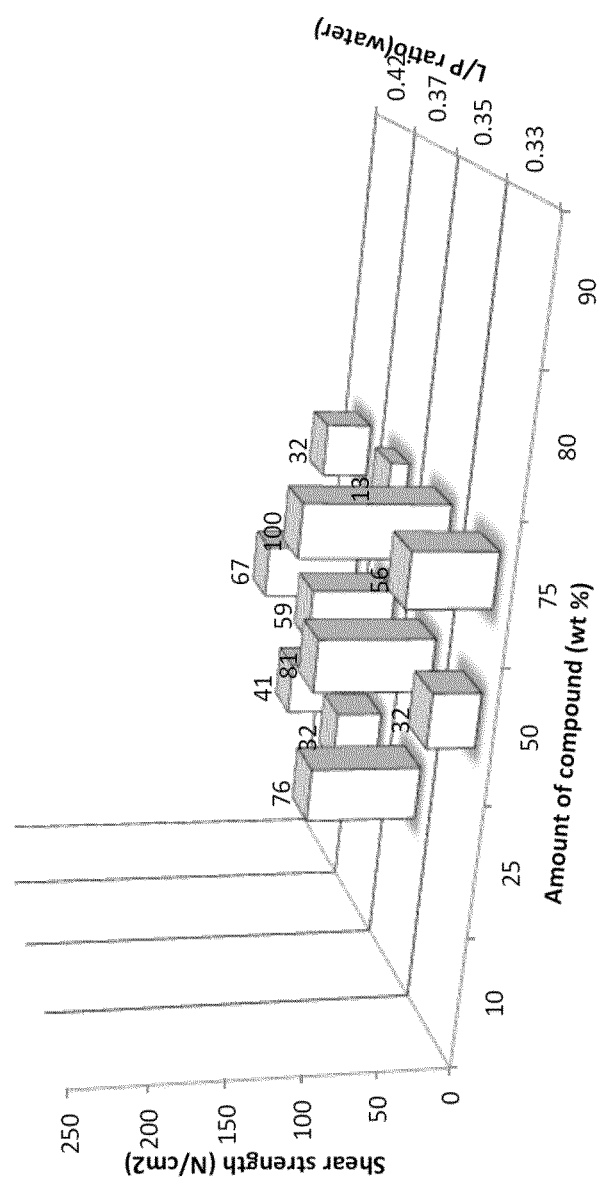
FIG. 4. Chemical composition chart (hard tissue). Cortical shear adhesive strength (for bone-to-bone adhesion) by nucleotide content (mixed bases and chain length) (wt %) and water content (L/P ratio), after 16-24 hours in 100% humidity, 37° C.

The results are disclosed in FIG. 4.

Compositions were prepared by premixing the calcium salt α-TCP powders (0.06 g, with 90% of particle size distribution below 75 μm) and phospho(enol)pyruvate (0.02 g) and by stirring with a spatula. Distilled water (0.028 ml, 25.9 wt % of the total weight) containing 22% (w/v) sodium citrate retardant was then added to the premixture and mixed by stirring for 10-20 seconds. L/P ratio of 0.35.

The composition was spread onto a cortical cube surface (1 cm×1 cm), to approximately 0.1-1 mm thickness with a spatula, sealed with manual clips, and stored in a humid sealed container kept at 37C, within 60 seconds of adding the liquid. The mechanical testing was done using a Shimadzu AGS-X machine, with trapezium liteX software, at a crosshead speed of 1 mm/minute. After testing the surface area of each cube that was covered with adhesive was measured with calipers and the recorded peak force was divided by the surface area to produce force per surface area (N/cm2).

Figure 5:
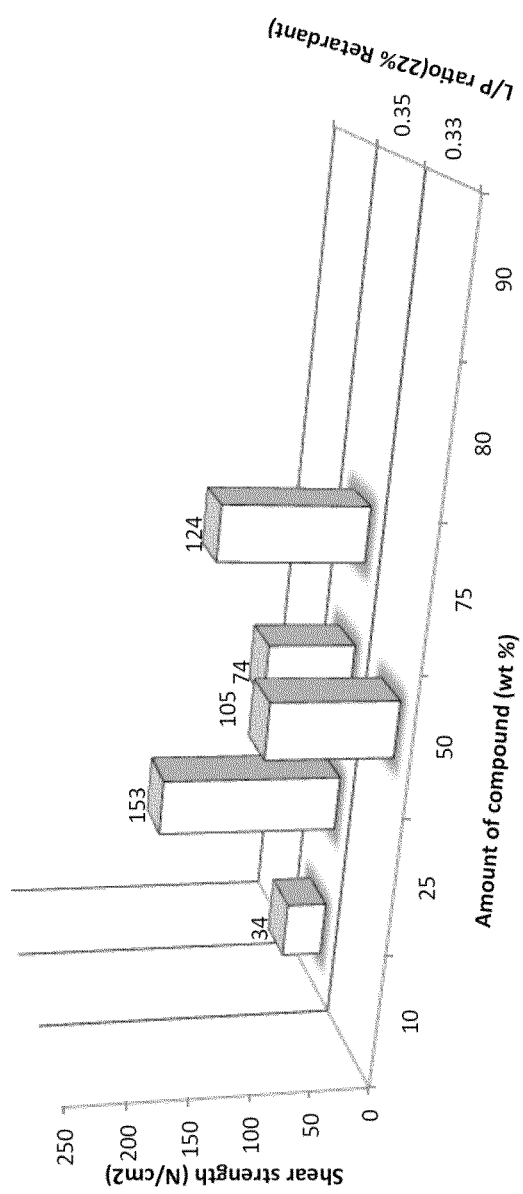
FIG. 5. Chemical composition chart (hard tissue). Cortical shear adhesive strength (for bone-to-bone adhesion) by phospho(enol)pyruvate content (mixed bases and chain length) (wt %) and water content (L/P ratio), after 16-24 hours in 100% humidity, 37° C.

The results are disclosed in FIG. 5.

Compositions were prepared by premixing the calcium salt α-TCP powders (0.06 g, with 90% of particle size distribution below 75 μm) and phosphocreatine (0.02 g) and by stirring with a spatula. Distilled water (0.020 ml, 20.00 wt % of the total weight) was then added to the premixture and mixed by stirring for 10-20 seconds.

The composition was spread onto a cortical cube surface (1 cm×1 cm), to approximately 0.1-1 mm thickness with a spatula, sealed with manual clips, and stored in a humid sealed container kept at 37C, within 60 seconds of adding the liquid. After 6, 12 or 1000-1500 minutes the samples were submerged in water, kept at 37° C., until a at least 16 hours had passed since the adhesive was mixed. The mechanical testing was done using a Shimadzu AGS-X machine, with trapezium liteX software, at a crosshead speed of 1 mm/minute. After testing the surface area of each cube that was covered with adhesive was measured with calipers and the recorded peak force was divided by the surface area to produce force per surface area (N/cm2).

The results are disclosed in FIG. 6.

Compositions were prepared by premixing phosphocreatine (0.02 g) with the calcium salt (α-TCP powder 0.06 g, with 90% of particle size distribution below 75 μm; tetracalcium phosphate powder 0.06, with 90% of particle size distribution below 750 μm; or calcium silicate in the form of Portland cement powder (mixture of di- and tricalcium silicates where the major elements are $SiO_2$ (19.5%), $Al_2O_3$ (5.2%) and CaO (63.9%)) 0.06 g, with 90% of particle size distribution below 10 μm) and and by stirring with a spatula. Distilled water (0.020 ml, 20.00 wt % of the total weight) was then added to the premixture and mixed by stirring for 10-20 seconds.

The composition was spread onto a cortical cube surface (1 cm×1 cm), to approximately 0.1-1 mm thickness with a spatula, sealed with manual clips, and stored in a humid sealed container kept at 37C, within 60 seconds of adding the liquid. The mechanical testing was done using a Shimadzu AGS-X machine, with trapezium liteX software, at a crosshead speed of 1 mm/minute. After testing the surface area of each cube that was covered with adhesive was measured with calipers and the recorded peak force was divided by the surface area to produce force per surface area (N/cm2).

The results are disclosed in FIG. 7.

The invention claimed is:

1. An aqueous composition comprising:
   a. an aqueous solution;
   b. a calcium phosphate compound wherein the calcium phosphate is α-TCP;
   c. an additive compound selected from phosphocreatine, wherein the carboxylic acid of the phosphocreatine may be in acid form or the corresponding salt;
   wherein the calcium phosphate compound represents 10-90 wt % and the additive compound represents 10-90 wt % of the solid content in the composition, wherein the composition comprises an acid, said acid optionally being the carboxylic acid of the additive compound, and has an acid concentration of 1.0-4.0M, and wherein the liquid/powder (L/P) ratio is 0.16-0.45.

2. The aqueous composition according to claim 1, wherein the composition further comprises an accelerator or retardant which is sodium citrate.

3. The aqueous composition according to claim 1, wherein the amount of the additive compound is 25-75 wt %.

4. The aqueous composition according to claim 1, wherein the L/P ratio is 0.20-0.35.

5. A biological tissue adhesive comprising the composition according to claim 1.

6. A bone filler comprising the composition according to claim 1.

7. A dental implant comprising the composition according to claim 1.

8. A method of adhering a first tissue to a second surface using the tissue adhesive according to claim 5 comprising:
   a. applying the tissue adhesive according to claim 5 to the first tissue or to the second surface and optionally leave it for a period of time of about 20 seconds to about 60 seconds;
   b. bringing the first tissue and the second surface into contact with each other;
   c. optionally applying a pressure on the first and second tissue for a period of time of about 1 to about 3 minutes; and
   d. letting the tissue adhesive cure.

9. A kit for preparing the composition according to claim 1 comprising at least two containers wherein any one container in the kit can contain any of the aqueous solution, the additive compound, the calcium phosphate compound or a combination thereof, with the proviso that both the additive compound and the calcium phosphate compound cannot be present in the same container as the aqueous solution; and
   wherein the amount of aqueous solution, additive compound, calcium phosphate compound in the containers is such that when mixed the composition according to claim 1 is obtained.

10. The aqueous composition according to claim 1 wherein the L/P ratio is 0.20-0.30.

11. The aqueous composition according to claim 2, wherein the sodium citrate is in the range of 5-66% weight/volume.

* * * * *

UNITED STATES PATENT AND TRADEMARK OFFICE
CERTIFICATE OF CORRECTION

| | |
|---|---|
| PATENT NO. | : 11,925,722 B2 |
| APPLICATION NO. | : 16/767579 |
| DATED | : March 12, 2024 |
| INVENTOR(S) | : Philip Procter et al. |

It is certified that error appears in the above-identified patent and that said Letters Patent is hereby corrected as shown below:

On the Title Page

Item (71) Applicant:
"GPBIO LTD., Limerick (IE)" should read --BIOMIMETIC INNOVATIONS LIMITED, Shannon Co. Clare (IE)--

Signed and Sealed this
Fourteenth Day of May, 2024

Katherine Kelly Vidal
*Director of the United States Patent and Trademark Office*